(12) United States Patent
Wang et al.

(10) Patent No.: US 7,543,588 B2
(45) Date of Patent: *Jun. 9, 2009

(54) MULTI-FUNCTIONAL SURGICAL CONTROL SYSTEM SWITCHING INTERFACE

(75) Inventors: Yulun Wang, Goleta, CA (US); Charles S. Jordan, Santa Barbara, CA (US); Darrin R. Uecker, Santa Barbara, CA (US)

(73) Assignee: Intuitive Surgical, Inc., Sunnyvale, CA (US)

( * ) Notice: Subject to any disclaimer, the term of this patent is extended or adjusted under 35 U.S.C. 154(b) by 139 days.

This patent is subject to a terminal disclaimer.

(21) Appl. No.: 11/473,349

(22) Filed: Jun. 21, 2006

(65) Prior Publication Data

US 2006/0241575 A1 Oct. 26, 2006

Related U.S. Application Data

(63) Continuation of application No. 10/722,837, filed on Nov. 26, 2003, now Pat. No. 7,097,640, which is a continuation of application No. 08/929,024, filed on Sep. 15, 1997, now abandoned, which is a continuation of application No. 08/771,885, filed on Dec. 23, 1996, now abandoned, which is a continuation of application No. 08/669,629, filed on Jun. 24, 1996, now abandoned.

(51) Int. Cl.
 *A61B 19/00* (2006.01)
(52) U.S. Cl. .............. 128/898; 606/10; 606/41; 704/200; 704/275; 381/110
(58) Field of Classification Search ............. 606/10–18, 606/32–52; 607/88, 89, 96, 101, 115; 128/898; 704/3, 4, 200–210, 230, 233, 251–255, 270, 704/275; 901/2–9, 30, 36, 46; 600/101–104, 600/106–109, 114, 118; 381/110; 414/2
See application file for complete search history.

(56) References Cited

U.S. PATENT DOCUMENTS 977,825 A 12/1910 Murphy (Continued)

FOREIGN PATENT DOCUMENTS

DE 9204118.3 7/1992

(Continued)

OTHER PUBLICATIONS

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

(Continued)

*Primary Examiner*—Ahmed M Farah

(57) ABSTRACT

An interface which allows a surgeon to operate multiple surgical devices from a single input device. The input device may be a foot pedal that provides output signals to actuate a number of different surgical devices. The surgical devices may include a robotic arm, a laser, an electrocautery device, or an operating table. The interface has an input channel that is coupled to the input device and a plurality of output channels that are coupled to the surgical devices. The interface also has a select input channel which can receive input commands to switch the input channel to one of the output channels. The select channel may be coupled to a speech interface that allows the surgeon to select one of the surgical devices with a voice command. The surgeon can operate any device by providing an input command which switches the input channel to the desired output channel.

7 Claims, 1 Drawing Sheet

U.S. PATENT DOCUMENTS

| | | | |
|---|---|---|---|
| 3,171,549 A | 3/1965 | Orloff | |
| 3,280,991 A | 10/1966 | Melton et al. | |
| 4,058,001 A | 11/1977 | Waxman | |
| 4,128,880 A | 12/1978 | Cray, Jr. | |
| 4,158,750 A | 6/1979 | Sakoe et al. | |
| 4,207,959 A | 6/1980 | Youdin et al. | |
| 4,216,462 A | 8/1980 | McGrath et al. | |
| 4,221,997 A | 9/1980 | Flemming | |
| 4,367,998 A | 1/1983 | Causer | |
| 4,401,852 A | 8/1983 | Noso et al. | |
| 4,456,961 A | 6/1984 | Price et al. | |
| 4,460,302 A | 7/1984 | Moreau et al. | |
| 4,474,174 A | 10/1984 | Petruzzi | |
| 4,491,135 A | 1/1985 | Klein | |
| 4,503,854 A | 3/1985 | Jako | |
| 4,517,963 A | 5/1985 | Michel | |
| 4,523,884 A | 6/1985 | Clement et al. | |
| 4,586,398 A | 5/1986 | Yindra | |
| 4,604,016 A | 8/1986 | Joyce | |
| 4,616,637 A | 10/1986 | Caspari et al. | |
| 4,624,011 A | 11/1986 | Watanabe | |
| 4,633,389 A | 12/1986 | Tanaka et al. | |
| 4,635,292 A | 1/1987 | Mori et al. | |
| 4,641,292 A | 2/1987 | Tunnell et al. | |
| 4,655,257 A | 4/1987 | Iwashita | |
| 4,672,963 A | 6/1987 | Barken | |
| 4,676,243 A | 6/1987 | Clayman | |
| 4,728,974 A | 3/1988 | Nio et al. | |
| 4,750,136 A | 6/1988 | Arpin | |
| 4,762,455 A | 8/1988 | Coughlan et al. | |
| 4,776,016 A | 10/1988 | Hansen | |
| 4,791,934 A | 12/1988 | Brunnett | |
| 4,791,940 A | 12/1988 | Hirschfeld | |
| 4,794,912 A | 1/1989 | Lia | |
| 4,807,273 A | 2/1989 | Haendle | |
| 4,815,006 A | 3/1989 | Andersson et al. | |
| 4,815,450 A | 3/1989 | Patel | |
| 4,817,050 A | 3/1989 | Komastu | |
| 4,837,734 A | 6/1989 | Ichikawa et al. | |
| 4,852,083 A | 7/1989 | Niehaus et al. | |
| 4,853,874 A | 8/1989 | Iwamoto et al. | |
| 4,854,301 A | 8/1989 | Nakajima | |
| 4,860,215 A | 8/1989 | Seraji | |
| 4,863,133 A | 9/1989 | Bonnel | |
| 4,883,400 A | 11/1989 | Kuban et al. | |
| 4,930,494 A | 6/1990 | Takehana et al. | |
| 4,945,479 A | 7/1990 | Rusterholz et al. | |
| 4,949,717 A | 8/1990 | Shaw | |
| 4,954,952 A | 9/1990 | Ubhayakar et al. | |
| 4,965,417 A | 10/1990 | Massie | |
| 4,969,709 A | 11/1990 | Sogawa et al. | |
| 4,969,890 A | 11/1990 | Sugita et al. | |
| 4,979,933 A | 12/1990 | Runge | |
| 4,979,949 A | 12/1990 | Matsen, III et al. | |
| 4,980,626 A | 12/1990 | Hess et al. | |
| 4,989,253 A | 1/1991 | Liang et al. | |
| 4,996,975 A | 3/1991 | Nakamura | |
| 5,019,968 A | 5/1991 | Wang et al. | |
| 5,020,001 A | 5/1991 | Yamamoto et al. | |
| 5,065,741 A | 11/1991 | Uchiyama et al. | |
| 5,078,140 A | 1/1992 | Kwoh | |
| 5,086,401 A | 2/1992 | Glassman et al. | |
| 5,091,656 A | 2/1992 | Gahn | |
| 5,097,829 A | 3/1992 | Quisenberry | |
| 5,097,839 A | 3/1992 | Allen | |
| 5,098,426 A | 3/1992 | Sklar et al. | |
| 5,105,367 A | 4/1992 | Tsuchihashi et al. | |
| 5,109,499 A | 4/1992 | Inagami et al. | |
| 5,123,095 A | 6/1992 | Papadopulos et al. | |
| 5,131,105 A | 7/1992 | Harrawood et al. | |
| 5,142,930 A | 9/1992 | Allen et al. | |
| 5,145,227 A | 9/1992 | Monford, Jr. | |
| 5,166,513 A | 11/1992 | Keenan et al. | |
| 5,175,694 A | 12/1992 | Amato | |
| 5,182,641 A | 1/1993 | Diner et al. | |
| 5,184,601 A | 2/1993 | Putman | |
| 5,187,574 A | 2/1993 | Kosemura et al. | |
| 5,196,688 A | 3/1993 | Hesse et al. | |
| 5,201,325 A | 4/1993 | McEwen et al. | |
| 5,201,743 A | 4/1993 | Haber et al. | |
| 5,217,003 A | 6/1993 | Wilk | |
| 5,221,283 A | 6/1993 | Chang | |
| 5,228,429 A | 7/1993 | Hatano | |
| 5,230,023 A | 7/1993 | Nakano | |
| 5,230,623 A | 7/1993 | Guthrie et al. | |
| 5,236,432 A | 8/1993 | Matsen, III et al. | |
| 5,249,121 A | 9/1993 | Baum et al. | |
| 5,251,127 A | 10/1993 | Raab | |
| 5,257,999 A | 11/1993 | Slanetz, Jr. | |
| 5,271,384 A | 12/1993 | McEwen et al. | |
| 5,274,862 A | 1/1994 | Palmer, Jr. et al. | |
| 5,279,309 A | 1/1994 | Taylor et al. | |
| 5,282,806 A | 2/1994 | Haber | |
| 5,289,273 A | 2/1994 | Lang | |
| 5,289,365 A | 2/1994 | Caldwell et al. | |
| 5,299,288 A | 3/1994 | Glassman et al. | |
| 5,300,926 A | 4/1994 | Stoeckl | |
| 5,303,148 A | 4/1994 | Mattson et al. | |
| 5,304,185 A | 4/1994 | Taylor | |
| 5,305,203 A | 4/1994 | Raab | |
| 5,305,427 A | 4/1994 | Nagata | |
| 5,309,717 A | 5/1994 | Minch | |
| 5,313,306 A | 5/1994 | Kuban et al. | |
| 5,320,630 A | 6/1994 | Ahmed | |
| 5,335,313 A | 8/1994 | Douglas | |
| 5,337,732 A | 8/1994 | Grundfest et al. | |
| 5,339,799 A | 8/1994 | Kami et al. | |
| 5,343,385 A | 8/1994 | Joskowicz et al. | |
| 5,343,391 A | 8/1994 | Mushabac | |
| 5,345,538 A | 9/1994 | Narayannan | |
| 5,357,962 A | 10/1994 | Green | |
| 5,368,015 A | 11/1994 | Wilk | |
| 5,368,428 A | 11/1994 | Hussey et al. | |
| 5,371,536 A | 12/1994 | Yamaguchi | |
| 5,372,147 A | 12/1994 | Lathrop, Jr. et al. | |
| 5,382,885 A | 1/1995 | Salcudean et al. | |
| 5,388,987 A | 2/1995 | Badoz et al. | |
| 5,395,369 A | 3/1995 | McBrayer et al. | |
| 5,397,323 A | 3/1995 | Taylor et al. | |
| 5,402,801 A | 4/1995 | Taylor | |
| 5,403,319 A | 4/1995 | Matsen, III et al. | |
| 5,408,409 A | 4/1995 | Glassman et al. | |
| 5,410,638 A | 4/1995 | Colgate et al. | |
| 5,417,210 A | 5/1995 | Funda et al. | |
| 5,417,701 A | 5/1995 | Holmes | |
| 5,422,521 A | 6/1995 | Neer et al. | |
| 5,431,645 A | 7/1995 | Smith et al. | |
| 5,434,457 A | 7/1995 | Josephs et al. | |
| 5,436,542 A | 7/1995 | Petelin et al. | |
| 5,442,728 A | 8/1995 | Kaufman et al. | |
| 5,443,484 A | 8/1995 | Kirsch et al. | |
| 5,445,166 A | 8/1995 | Taylor | |
| 5,451,924 A | 9/1995 | Massimino et al. | |
| 5,455,766 A | 10/1995 | Schaller et al. | |
| 5,458,547 A | 10/1995 | Teraoka et al. | |
| 5,458,574 A | 10/1995 | Machold et al. | |
| 5,476,010 A | 12/1995 | Fleming et al. | |
| 5,482,073 A | 1/1996 | Winnie et al. | |
| 5,490,117 A | 2/1996 | Oda | |
| 5,490,843 A | 2/1996 | Hildwein et al. | |
| 5,500,854 A | 3/1996 | Uotila | |
| 5,506,912 A | 4/1996 | Nagasaki et al. | |
| 5,511,256 A | 4/1996 | Capaldi | |
| 5,512,919 A | 4/1996 | Araki | |

| | | |
|---|---|---|
| 5,515,478 A | 5/1996 | Wang |
| 5,544,654 A | 8/1996 | Murphy et al. |
| 5,553,198 A | 9/1996 | Wang et al. |
| 5,562,503 A | 10/1996 | Ellman et al. |
| 5,566,272 A | 10/1996 | Brems et al. |
| 5,571,110 A | 11/1996 | Matsen, III et al. |
| 5,572,999 A | 11/1996 | Funda et al. |
| 5,609,560 A | 3/1997 | Ichikawa et al. |
| 5,626,595 A | 5/1997 | Sklar et al. |
| 5,627,584 A | 5/1997 | Nishikori et al. |
| 5,629,594 A | 5/1997 | Jacobus et al. |
| 5,630,431 A | 5/1997 | Taylor |
| 5,631,973 A | 5/1997 | Green |
| 5,636,259 A | 6/1997 | Khutoryansky et al. |
| 5,640,953 A | 6/1997 | Bishop et al. |
| 5,649,956 A | 7/1997 | Jensen et al. |
| 5,657,429 A | 8/1997 | Wang et al. |
| 5,658,250 A | 8/1997 | Blomquist et al. |
| 5,676,673 A | 10/1997 | Ferre et al. |
| 5,695,500 A | 12/1997 | Taylor et al. |
| 5,696,574 A | 12/1997 | Schwaegerle |
| 5,696,837 A | 12/1997 | Green |
| 5,713,350 A | 2/1998 | Yokota et al. |
| 5,715,548 A | 2/1998 | Weismiller et al. |
| 5,715,823 A | 2/1998 | Wood |
| 5,718,038 A | 2/1998 | Takiar et al. |
| 5,727,569 A | 3/1998 | Benetti et al. |
| 5,729,659 A | 3/1998 | Potter |
| 5,735,290 A | 4/1998 | Sterman et al. |
| 5,737,711 A | 4/1998 | Abe |
| 5,749,362 A | 5/1998 | Fund et al. |
| 5,754,741 A | 5/1998 | Wang et al. |
| 5,762,458 A | 6/1998 | Wang et al. |
| 5,771,511 A | 6/1998 | Kummer et al. |
| 5,774,741 A | 6/1998 | Choi |
| 5,774,841 A | 6/1998 | Salazar et al. |
| 5,776,126 A | 7/1998 | Wilk et al. |
| 5,779,623 A | 7/1998 | Bonnell |
| 5,788,688 A | 8/1998 | Bauer et al. |
| 5,792,135 A | 8/1998 | Madhani et al. |
| 5,792,178 A | 8/1998 | Welch et al. |
| 5,797,900 A | 8/1998 | Madhani et al. |
| 5,800,423 A | 9/1998 | Jensen |
| 5,802,467 A | 9/1998 | Salazar et al. |
| 5,807,284 A | 9/1998 | Foxlin |
| 5,807,377 A | 9/1998 | Madhani et al. |
| 5,807,378 A | 9/1998 | Jensen et al. |
| 5,808,665 A | 9/1998 | Green |
| 5,809,591 A | 9/1998 | Capaldi et al. |
| 5,810,880 A | 9/1998 | Jensen et al. |
| 5,812,978 A | 9/1998 | Nolan |
| 5,813,813 A | 9/1998 | Daum et al. |
| 5,814,038 A | 9/1998 | Jensen et al. |
| 5,817,084 A | 10/1998 | Jensen |
| 5,825,982 A | 10/1998 | Wright et al. |
| 5,836,869 A | 11/1998 | Kudo et al. |
| 5,841,950 A | 11/1998 | Wang et al. |
| 5,842,173 A | 11/1998 | Strum et al. |
| 5,844,824 A | 12/1998 | Newman et al. |
| 5,855,583 A | 1/1999 | Wang et al. |
| 5,857,967 A | 1/1999 | Frid et al. |
| 5,859,934 A | 1/1999 | Green |
| 5,860,995 A | 1/1999 | Berkelaar |
| 5,876,325 A | 3/1999 | Mizuno et al. |
| 5,877,819 A | 3/1999 | Branson |
| 5,878,193 A | 3/1999 | Wang et al. |
| 5,882,206 A | 3/1999 | Gillio |
| 5,884,350 A | 3/1999 | Kurze |
| 5,887,121 A | 3/1999 | Funda et al. |
| 5,895,461 A | 4/1999 | De La Huerga |
| 5,897,498 A | 4/1999 | Canfield et al. |
| 5,924,074 A | 7/1999 | Evans |
| 5,931,832 A | 8/1999 | Jensen |
| 5,950,629 A | 9/1999 | Taylor et al. |
| 5,970,457 A | 10/1999 | Brant et al. |
| 5,971,976 A | 10/1999 | Wang et al. |
| 5,976,156 A | 11/1999 | Taylor et al. |
| 6,024,695 A | 2/2000 | Taylor et al. |
| 6,080,181 A | 6/2000 | Jensen et al. |
| 6,102,850 A | 8/2000 | Wang et al. |
| 6,201,984 B1 | 3/2001 | Funda et al. |
| 6,224,542 B1 | 5/2001 | Chang et al. |
| 6,278,975 B1 * | 8/2001 | Brant et al. ................. 704/275 |
| 6,463,361 B1 | 10/2002 | Wang et al. |
| 6,496,099 B2 | 12/2002 | Wang et al. |
| 6,642,836 B1 | 11/2003 | Wang et al. |
| 6,646,541 B1 | 11/2003 | Wang et al. |
| 6,788,999 B2 | 9/2004 | Green |
| 6,850,817 B1 | 2/2005 | Green |
| 7,097,640 B2 * | 8/2006 | Wang et al. ................... 606/10 |

FOREIGN PATENT DOCUMENTS

| | | |
|---|---|---|
| DE | 4310842 | 1/1995 |
| EP | 0239409 | 9/1987 |
| EP | 0424687 | 5/1991 |
| EP | 0776738 | 6/1997 |
| FR | 2 642 882 | 8/1990 |
| WO | 91/04711 | 4/1991 |
| WO | 92/20295 | 11/1992 |
| WO | 93/13916 | 7/1993 |
| WO | 94/18881 | 9/1994 |
| WO | 94/26167 | 11/1994 |
| WO | 95/01757 | 1/1995 |
| WO | 96/09587 | 3/1996 |
| WO | 97/15240 | 5/1997 |
| WO | 98/25666 | 6/1998 |
| WO | 99/21165 | 4/1999 |
| WO | 99/42029 | 8/1999 |

OTHER PUBLICATIONS

Abstract of a presentation "3-D Vision Technology Applied to Advanced Minimally Invasive Surgery Systems" given at the 3rd World Congress of Endoscopic Surgery in Bordeaux, Jun. 18-20, 1992 (1 page total).

Abstract of a presentation "A Pneumatic Controlled Sewing Device for Endoscopic Application the MIS Sewing Instrument MSI" given at the 3rd World Congress of Endoscopic Surgery in Bordeaux, Jun. 18-20, 1992 (1 page total).

Abstract of a presentation "Concept and Experimental Application of a Surgical Robot System and Steerable MIS Instrument SMI" given at the 3$^{rd}$ World Congress of Endoscopic Surgery in Bordeaux, Jun. 18-29, 1992 (1 page total).

Abstract of a presentation given at the 3rd World Congress of Endoscopic Surgery in Bordeaux (Jun. 18 to 20, 1992), entitled "Session 15/2" (1 page total).

Abstract of a presentation given at the 3rd World Congress of Endoscopic Surgery in Bordeaux (Jun. 18 to 20, 1992), entitled "Session 15/4" (1 page total).

Abstract of a presentation given at the 3rd World Congress of Endoscopic Surgery in Bordeaux (Jun. 18 to 20, 1992), entitled "Session 15/5" (1 page total).

Abstract of a presentation given at the 3rd World Congress of Endoscopic Surgery in Bordeaux, Jun. 18-20, 1992, entitled "Session 15/1" (1 page total).

Alexander, "A Survey Study of Teleoperators, Robotics, and Remote Systems Technology", Remotely Manned Systems—Exploration and Operation in Space, California Institute of Technology 1973.

Alexander, "Impacts of Telemation on Modern Society", On the Theory and Practice of Robots and Manipulators vol. II, 1974.

Bejczy, "Controlling Remote Manipulators through Kinesthetic Coupling," Computers in Mechanical Engineering 1983, pp. 48-60.

Besant et at., Abstract of a presentation "Camera Control for Laparoscopic Surgery by Speech-Recognizing Robot: Constant Attention and Better Use of Personnel," given at the 3rd World Congress of Endoscopic Surgery in Bordeaux, Jun. 18-20, 1992 (1 page total).

Charles et al., "Design of a Surgeon-Machine Interface for Teleoperated Microsurgery," IEEE 1989 (3 pages total).

Colgate, "Power and Impedance Scaling in Bilateral Manipulation," IEEE, 1991, pp. 2292-2297.

Corcoran, "Robots for the Operating Room," The New York Times, Sunday Jul. 19, 1992, Section 3, p. 9, col. 1 (2 pages total).

Das et al., "Kinematic Control and Visual Display of Redundant Teleoperators," IEEE 1989 pp. 1072-1077.

Dolan et al., "A Robot in an Operating Room: A Bull in a China Shop," IEEE, 1987, pp. 1096-1097.

Fu et al., "Robotics: Control, Sensing, Vision and Intelligence", McGraw-Hill Book Company, 1987, Table of Contents (5 pages total).

Gayed et al., "An Advanced Control Micromanipulator for Surgical Applications," Systems Science vol. 13, 1987, pp. 23-34.

Green et al., Abstract of a presentation "Telepresence: Advanced Teleoperator Technology for Minimally Invasive Surgery," given at "Medicine meets virtual reality" symposium in San Diego, Jun. 4-7, 1992 (20 pages total).

Green et al., Abstract of a presentation "Telepresence: Advanced Teleoperator Technology for Minimally Invasive Surgery," given at the 3rd World Congress of Endoscopic Surgery in Bordeaux, Jun. 18-20, 1992 (2 pages total).

Green, Statutory Declaration of Dr. Philip S. Green, presenter of the video entitled "Telepresence Surgery—The Future of Minimally Invasive Medicine" (32 page total).

Guerrouad et al., "S.M.O.S.: Stereotaxical Microtelemanipulator for Ocular Surgery," IEEE, 1989, pp. 879-880.

Guerrouad, "Voice Control in the Surgery Room," IEEE Engineering in Medicine & Biology Society 11th Annual International Conference 1989 (2 pages total).

Inoue et al., "Six-axis Bilateral Control of an Articulated Slave Manipulator Using a Cartesian Master Manipulator," Advanced Robotics, 4, No. 2, 1990, pp. 139-150.

Kazerooni, "Human/Robot Interaction via the Transfer of Power and Information Signals—Part I: Dynamics and Control Analysis," IEEE, 1989, pp. 1632-1640.

Kazerooni, "Human/Robot Interaction via the Transfer of Power and Information Signals—Part II: An Experimental Analysis," IEEE, 1989, pp. 1641-1647.

Krishnan et al., Abstract of a presentation "Design Considerations of a New Generation Endoscope Using Robotics and Computer Vision Technology," given at the 3rd World Congress of Endoscopic Surgery in Bordeaux, Jun. 18-20, 1992 (1 page total).

Lavallee, "A New System for Computer Assisted Neurosurgery," IEEE, 1989, vol. 11, pp. 926-927.

Mair, Industrial Robotics, Prentice Hall, 1988, pp. 41-43, 49-50, 54, 203-209.

Majima et al., "On a Micro-Manipulator for Medical Application—Stability Consideration of its Bilateral Controller," Mechatronics, 1991, pp. 293-309.

NASA, "Anthropomorphic Remote Manipulator", NASA Tech Briefs, 1991 (1 page total).

Preising et al., "A Literature Review: Robots in Medicine," IEEE, Jun. 1991, pp. 13-22 & 71.

Rasor et al., "Endocorporeal Surgery Using Remote Manipulators", Remotely Manned Systems—Exploration and Operation in Space, California Institute of Technology 1973.

Sabatini et al., "Force Feedback-Based Telemicromanipulation for Robot Surgery on Soft Tissues," IEEE, 1989, pp. 890-891.

Stryker Endoscopy, "Sidne", Operating and Maintenance Manual, 33 pages total.

Taubes, "Surgery in Cyberspace," Discover Magazine, Dec. 1994, pp. 85-92.

Taylor et al., Taming the Bull: Safety in a Precise Surgical Robot, IEEE, 1991, pp. 865-871.

Tejima, "A New Microsurgical Robot System for Corneal Transplantation," Precision Machinery, 1988 vol. 2, pp. 1-9.

Tendick et al., "Analysis of the Surgeon's Grasp for Telerobotic Surgical Manipulation," IEEE, 1989, pp. 914-915.

Thring, "Robots and Telechirs: Manipulator with Memory: Remote Manipulators: Machine Limbs for the Handicapped," Wiley & Sons, 1983 (26 pages total).

Transcript of a video presented by SRI at the 3rd World Congress of Endoscopic Surgery in Bordeaux on Jun. 18-20, 1992, in Washington on Apr. 9, 1992, and in San Diego, CA on Jun. 4-7, 1992 entitled Telepresence Surgery—The Future of Minimally Invasive Medicine (3 pages total).

Trevelyan et al., "Motion Control for a Sheep Shearing Robot," Proceedings of the 1st International Symposium on Robotics Research, MIT, Cambridge, Massachusetts, USA, 1983, pp. 175.

Vibet, "Properties of Master-Slave Robots," Motor-con, 1987, pp. 309-314.

Wilson et al., "Filmless PACS in a multiple facility environment," Proceedings of the Spie, Spie, Bellingham, VA, US vol. 2711, pp. 500-509 (XP002082137).

Wolf et al., "Student Reference Manual for Electronic Instrumentation Laboratories," Prentice Hall, New Jersey 1990, pp. 498 and 499.

* cited by examiner

MULTI-FUNCTIONAL SURGICAL CONTROL SYSTEM SWITCHING INTERFACE

CROSS REFERENCE TO RELATED APPLICATIONS

This application is a continuation of U.S. patent application Ser. No. 10/722,837, filed Nov. 26, 2003, now U.S. Pat. No. 7,097,640 which is a continuation of U.S. patent application Ser. No. 08/929,024, filed Sep. 15, 1997, now abandoned which is a continuation of U.S. patent application Ser. No. 08/771,885, filed Dec. 23, 1996, now abandoned, which is a continuation of U.S. patent application Ser. No. 08/669,629, filed Jun. 24, 1996, now abandoned, the full disclosures of which are incorporated herein by reference.

BACKGROUND OF THE INVENTION

1. Field of the Invention

The present invention generally relates to control systems. More particularly, the present invention relates to an interface that allows multiple surgical devices to be controlled from an input device, such as a foot pedal.

2. Description of Related Art

Many surgical procedures are performed with multiple instruments. For example, some laparoscopic procedures are performed utilizing a robotic arm system produced by Computer Motion, Inc. of Goleta, Calif. to hold and move an endoscope. The surgeon may also use a laser to cut tissue and an electrocautery device to cauterize the tissue. Each instrument has a unique control panel or foot pedal to operate the device. The surgeon must therefore depress one foot pedal to move the robotic arm and endoscope, depress a different foot pedal to actuate the electrocautery device, and manipulate yet another input device to energize the laser. Operating multiple input devices may distract the surgeon, thereby reducing the efficiency and safety of performing the procedure. It would therefore be desirable to provide an interface that would allow the surgeon to select and control multiple surgical devices from a single input device. Additionally, it is also desirable to provide an interface that would allow the surgeon to mutually exclusively select and control multiple surgical devices from an input device.

SUMMARY OF THE INVENTION

The present invention provides an interface for coupling an input device to a first surgical apparatus and a second surgical apparatus, the interface comprising:

(a) a first input channel coupled to the input device;

(b) a first output channel coupled to the first surgical apparatus;

(c) a second output channel coupled to the second surgical apparatus;

(d) a select channel configured to switch said first input channel between said first output channel and said second output channel.

The interface allows a surgeon to operate multiple surgical devices from a single input device. The input device may be a foot pedal that provides output signals to actuate a number of different surgical devices. The surgical devices may include a robotic arm system, a laser, an electrocautery device, or an operating table. The interface has an input channel that is coupled to the input device and a plurality of output channels that are coupled to the surgical devices. The interface also has a select channel which can receive input commands and correspondingly switch the input channel between one of the output channels. The select channel may be coupled to a speech interface that allows the surgeon to select one of the surgical devices with a voice command. The surgeon can then operate a specific device after providing an input or switching command which switches the input channel to the desired output channel and thereby connects the input device with the desired surgical device.

BRIEF DESCRIPTION OF THE DRAWINGS

The objects and advantages of the present invention will be readily apparent to those ordinarily skilled in the art after reviewing the following detailed description and accompanying drawings, wherein.

DETAILED DESCRIPTION OF THE INVENTION

Figure 1:
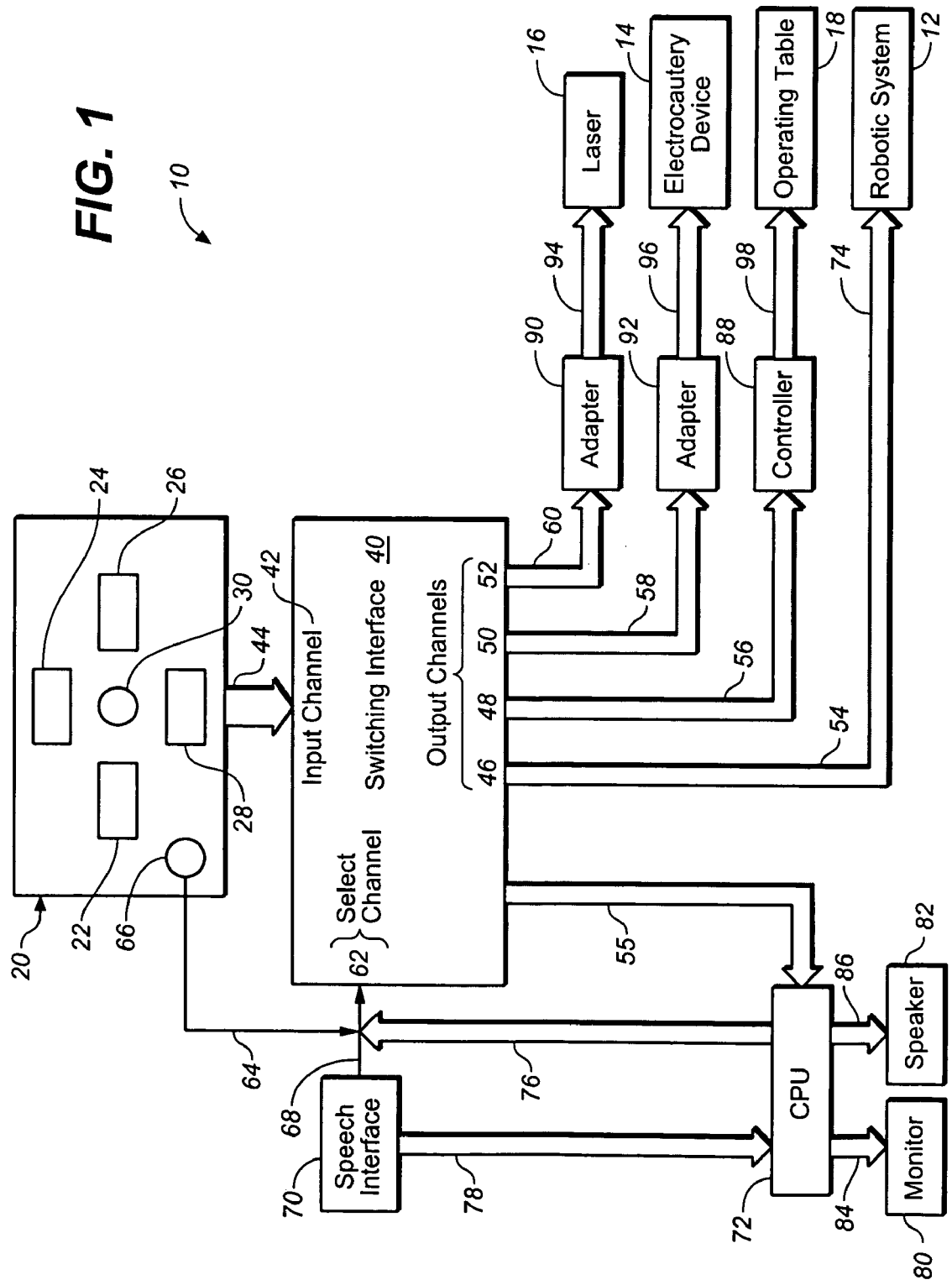
FIG. 1 is a schematic of a control system and interface in accordance with the present invention.

Referring to drawings more particularly by reference numbers, FIG. 1 shows a surgical system 10 in accordance with the present invention. The system 10 allows a surgeon to operate a number of different surgical devices 12, 14, 16 and 18 from a single input device 20. Providing a single input device reduces the complexity of operating the various devices and improves the efficiency of a surgical procedure performed by a surgeon.

Surgical device 12 may be a robotic arm which can hold and move a surgical instrument. The arm 12 may be a device such as that sold by Computer Motion, Inc. of Goleta, Calif. under the trademark AESOP. The arm 12 is commonly used to hold and move an endoscope within a patient. The system of the present invention allows the surgeon to control the operation of the robotic arm 12 through the input device 20.

Surgical device 14 may be an electrocautery device. Electrocautery devices typically have a bi-polar tip which carries a current that heats and denatures tissue. The device is typically coupled to an on-off switch to actuate the device and heat the tissue. The electrocautery device may also receive control signals to vary its power output. The system 10 of the present invention allows the surgeon to control the operation of the electrocautery device through the input device 20.

Surgical device 16 may be a laser. The laser 16 may be actuated through an on-off switch. Additionally, the power of the laser 16 may be controlled by control signals. The system 10 of the present invention allows the surgeon to control the operation of the laser 16 through the input device 20.

Device 18 may be an operating table. The operating table 18 may contain motors and mechanisms which adjust the position of the table. The present invention allows the surgeon to control the position of the table 18 through the input device 20. Although four surgical devices 12, 14, 16 and 18 are described, it is to be understood that other functions within the operating room may be controlled through the input device 20. By way of example, the system 10 may allow the surgeon to control the lighting and temperature of the operating room through the input device 20.

The input device 20 may be a foot pedal which has a plurality of buttons 22, 24, 26, 28 and 30 that can be depressed by the surgeon. Each button is typically associated with a specific control command of a surgical device. For example, when the input device 20 is controlling the robotic arm 12, depressing button 22 may move the arm in one direction and depressing button 26 may move the arm in an opposite direction. Likewise, when the electrocautery device 14 or laser 16 are coupled to the input device 20, depressing button 30 may energize the devices, and so forth and so on. Although a foot pedal is shown and described, it is to be understood that the input device 20 may be a hand controller, a speech interface which accepts voice commands from the surgeon, a cantilever pedal or other input devices which may be well known in the art of surgical device control.

The system 10 has a switching interface 40 which couples the input device 20 to the surgical devices 12, 14, 16 and 18. The interface 40 has an input channel 42 which is connected to the input device 20 by bus 44. The interface 40 also has a plurality of output channels 46, 48, 50 and 52 that are coupled to the surgical devices by busses 54, 56, 58, 60, 94, 96, 98 and which may have adapters or controllers disposed in electrical communication therewith and therebetween. Such adapters and controllers will be discussed in more detail hereinbelow.

Because each device 12, 14, 16, 18 may require specifically configured control signals for proper operation, adapters 90, 92 or a controller 88 may be placed intermediate and in electrical communication with a specific output channel and a specific surgical device. In the case of the robotic arm system 12, no adapter is necessary and as such, the robotic arm system 13 may be in direct connection with a specific output channel. The interface 40 couples the input channel 42 to one of the output channels 46, 48, 50 and 52.

The interface 40 has a select channel 62 which can switch the input channel 42 to a different output channel 46, 48, 50 or 52 so that the input device 20 can control any of the surgical devices. The interface 40 may be a multiplexor circuit constructed as an integrated circuit and placed on an ASIC. Alternatively, the interface 40 may be a plurality of solenoid actuated relays coupled to the select channel by a logic circuit. The interface 40 switches to a specific output channel in response to an input signal or switching signal on the select channel 62.

As depicted in FIG. 1, there may be several inputs to the select channel 62. Such inputs originate from the foot pedal 20, the speech interface 70 and the CPU 72. The interface 40 may have a multiplexing unit such that only one switching signal may be received at the select channel 62 at any one time, thus ensuring no substantial hardware conflicts. The prioritization of the input devices may be configured so the foot pedal has highest priority followed by the voice interface and the CPU. This is intended for example as the prioritization scheme may be employed to ensure the most efficient system. As such other prioritization schemes may be employed. The select channel 62 may sequentially connect the input channel to one of the output channels each time a switching signal is provided to the select channel 62. Alternatively, the select channel 62 may be addressable so that the interface 40 connects the input channel to a specific output channel when an address is provided to the select channel 62. Such addressing is known in the art of electrical switches.

The select channel 62 may be connected by line 64 to a dedicated button 66 on the foot pedal 20. The surgeon can switch surgical devices by depressing the button 66. Alternatively, the select channel 62 may be coupled by line 68 to a speech interface 70 which allows the surgeon to switch surgical devices with voice commands.

The system 10 may have a central processing unit (CPU) 72 which receives input signals from the input device 20 through the interface 40 and bus 55. The CPU 72 receives the input signals, and can ensure that no improper commands are being input at the controller. If this occurs, the CPU 72 may respond accordingly, either by sending a different switching signal to select channel 62, or by alerting the surgeon via a video monitor or speaker.

The CPU 72 can also provide output commands for the select channel 62 on bus 76 and receive input commands from the speech interface 70 on the same bi-directional bus 76. The CPU 72 may be coupled to a monitor 80 and/or a speaker 82 by buses 84 and 86, respectively. The monitor 80 may provide a visual indication of which surgical device is coupled to the input device 20. The monitor may also provide a menu of commands which can be selected by the surgeon either through the speech interface 70 or button 66. Alternatively, the surgeon could switch to a surgical device by selecting a command through a graphic user interface. The monitor 80 may also provide information regarding improper control signals sent to a specific surgical device 12, 14, 16, 18 and recognized by the CPU 72. Each device 12, 14, 16, 18 has a specific appropriate operating range, which is well known to the skilled artisan. As such, the CPU 72 may be programmed to recognize when the requested operation from the input device 20 is inappropriate and will then alert the surgeon either visually via the monitor 80 or audibly via the speaker 82. The speaker 82 may also provide an audio indication of which surgical device is coupled to the input device 20.

The system 10 may include a controller 88 which receives the input signals from the input device 20 and provides corresponding output signals to control the operating table 18. Likewise, the system may have adapters 90 and 92 which provide an interface between the input device 20 and the specific surgical instruments connected to the system.

In operation, the interface 40 initially couples the input device 20 to one of the surgical devices. The surgeon can control a different surgical device by generating an input command that is provided to the select channel 62. The input command switches the interface 40 so that the input device 20 is coupled to a different output channel and corresponding surgical device or adapter. What is thus provided is an interface 40 that allows a surgeon to select, operate and control a plurality of different surgical devices through a common input device 20.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A method comprising:
    receiving at a switching interface a first input from a mechanical input device, the first input selecting a first surgical apparatus;
    receiving at the switching interface a second input from a speech interface, the second input selecting a second surgical apparatus;
    determining that a conflict exists between the first input and the second input;
    determining a priority between the first input and the second input according to a specified prioritization scheme; and
    selecting one of the first surgical apparatus and second surgical apparatus according to the determined priority.

2. The method of claim 1, wherein the conflict exists between the first input and the second input when the first input and the second input are received at substantially the same time.

3. The method of claim 1, wherein the prioritization scheme identifies a particular input channel as having priority to the switching interface.

4. The method of claim 1, wherein the prioritization scheme identifies a particular input device as having priority to the switching interface.

5. A method comprising:
receiving a control input from a mechanical input device;
receiving a voice selection command;
converting the voice selection command to a command signal;
switching, responsive to the command signal, the control input to one of a first surgical apparatus or a second surgical apparatus to allow for control of a selected surgical apparatus using the mechanical input device; and
controlling the surgical apparatus including receiving one or more control inputs including a control input to vary a power of the selected surgical apparatus.

6. The method of claim 5, wherein the control input varies the power of a laser.

7. The method of claim 5, wherein the control input varies the power of an electrocautery device.

* * * * *